United States Patent [19]

Miyoshi

[11] Patent Number: 4,816,569
[45] Date of Patent: Mar. 28, 1989

[54] NUCLEOTIDE DERIVATIVE

[75] Inventor: Kenichi Miyoshi, Hiroshima, Japan

[73] Assignee: Wakunaga Seiyaku Kabushiki Kaisha, Osaka, Japan

[21] Appl. No.: 792,824

[22] Filed: Oct. 30, 1985

[30] Foreign Application Priority Data

Nov. 5, 1984 [JP] Japan .................. 59-232941

[51] Int. Cl.$^4$ .................. C07H 19/10; C07H 12/00
[52] U.S. Cl. .................. 536/29; 536/23; 536/27; 536/28
[58] Field of Search .................. 536/29

[56] References Cited

U.S. PATENT DOCUMENTS

| | | | |
|---|---|---|---|
| 4,086,417 | 4/1978 | Ishida et al. | 536/29 |
| 4,297,347 | 10/1981 | Katsunuma | 536/29 |
| 4,415,732 | 11/1983 | Caruthers et al. | 536/29 |
| 4,417,046 | 11/1983 | Hsiung | 536/29 |

Primary Examiner—Johnnie R. Brown
Assistant Examiner—L. Eric Crane
Attorney, Agent, or Firm—Oblon, Fisher, Spivak, McClelland & Maier

[57] ABSTRACT

A nucleotide of the formula [IV] shown below:

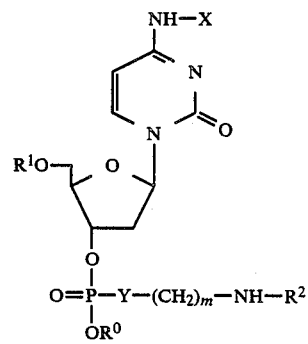

wherein: X is hydrogen or $-CO-(CH_2)_n-CO-R^3$; each of m and n is an integer up to 20; $R^0$ is a protective group of a phosphoric acid group, $R^1$ is hydrogen or a protective group for a 5'-hydroxyl group, $R^2$ is hydrogen or a protective group for an amino group, $R^3$ is a carrier having an amino group as the functional group and bound at this functional group in this compound, Y is oxygen atom ($-O-$) or an imino group ($-NH-$). This nucleotide, when the X is $-CO-(CH_2)_n-CO-R^3$, has a carrier ($R^3$) through a spacer ($-CO-(CH_2)_m-CO-$) on extension from the amino group of deoxycytidine and therefore can be used as the starting material, namely the resin, for synthesizing a 3'-aminated oligonucleotide according to the solid phase method.

15 Claims, 10 Drawing Sheets

NUCLEOTIDE DERIVATIVE

BACKGROUND OF THE INVENTION

1. Field of the art

This invention relates to a novel nucleotide derivative. More particularly, the present invention pertains to a nucleotide derivative in which a primary amino group has been introduced through an alkylene group on extension from the 3'-phosphate group of deoxycytidine, and which is bound to a carrier through a spacer to the amino group of cytosine.

2. Prior art

I have previously proposed oligonucleotide derivatives in which an aminoalkyl group has been introduced at 5'-ends (hereinafter referred to as 5'-end aminated oligonucleotide) (Japanese Patent Laid-Open Publications Nos. 93098/1984, 93099/1984 and 93100/1984). The 5'-aminated oligonucleotide can be bound to various labeling materials (or simply labels) and carriers through the amino group introduced. Examples of the labeling material may include biotin, 2,4-dinitrobenzene, fluorescent substances (rhodamine, fluorescein, etc.), enzyme proteins (horse radish peroxidase, alkali phosphatase, β-galactosidase) and metalated proteins (ferrictin, etc.). Among these, concerning biotin and 2,4-dinitrobenzene, I have already proposed oligonucleotide derivatives having these bound thereto and methods for preparation thereof (Japanese Patent Laid-Open Publication No. 148798/1984 and Japanese Patent Application No. 75878/1983). On the other hand, as the carrier, Sepharose, etc. may be considered, and the oligonucleotide derivatives bound to carriers (hereinafter called immobilized nucleotide) and preparation thereof have already been proposed by me (Japanese Patent Laid-Open Publication No. 27900/1984).

Examples of the uses of immobilized nucleotides may include isolation and purification of mRNA in general, isolation of mRNA having specific base sequence [J. Biochem., 81, 941 (1977)], separation of double-stranded DNA, isolation and purification of single-stranded DNA, synthesis of long chain oligonucleotides and isolation and purification of nucleic acid-concerned enzymes.

Also, oligonucleotide derivatives having as a label biotin or 2,4-dinitrobenzene bound thereto can be used as a non-radioactive affinity probe for detection of target genes, nucleic acid bindable proteins, etc., and utilized for the biotin-avidin technique [DNA, 3, 269–277 (1984), Nucleic Acids Research, 5, 363–384 (1978)], the enzyme immunoassay [Nucleic Acids Research, 10, 6789–6796 (1982), etc.], the fluorescent antibody technique [Nucleic Acids Research, 12, 1791–1810] and the electron microscope technique [the above Nucleic Acids Research, etc.]. See BIOMEDICAL BUSINESS INTERNATIONAL, 7. 78–79 (1984), Nature, 306, 5941 (1983), DNA, 2, 72 (1983), etc.

Thus, since oligonucleotides and derivatives thereof are of very great potential utilization value (Journal "BIOTECHNOLOGY", AUGUST (1983), published by NATURE PUBLISHING COMPANY), the establishment of a method of synthesizing the same and preparation of novel derivatives thereof are being urgently sought.

Accordingly, I have also proposed, subsequent to the above 5'-end aminated oligonucleotides, oligonucleotide derivatives in which an amino alkyl group has been introduced at the 3'-end (hereinafter called 3'-end aminated oligonucleotide) (Japanese Patent Applications Nos. 22474/1984 and 22475/1984). For the 3'-end aminated oligonucleotide, various uses may be considered similarly as for the above 5'-end aminated oligonucleotide, and it is also possible to utilize it in combination with the 5'-end aminated oligonucleotide as a compound forming a pair. However, since the 3'-end aminated oligonucleotide can be synthesized only by the liquid phase method, the following problems have been encountered.

(1) The reaction scale is large.

(2) In the respective steps of oligonucleotide synthesis (deprotection, condensation, etc.), purification of intermediates is required, and, additionally, the skill of an expert is required for the operation of oligonucleotide synthesis. As a result, much synthesis time and labor are necessary.

Thus, the development of a method for solving these various problems has been greatly desired.

SUMMARY OF THE INVENTION

An object of the present invention is to overcome the problems described above by providing a useful starting compound in the synthesis of a 3'-end aminated oligonucleotide and further by providing also a method for producing the compound by utilizing this compound.

The nucleotide according to the present invention is represented by the formula [IV] shown below.

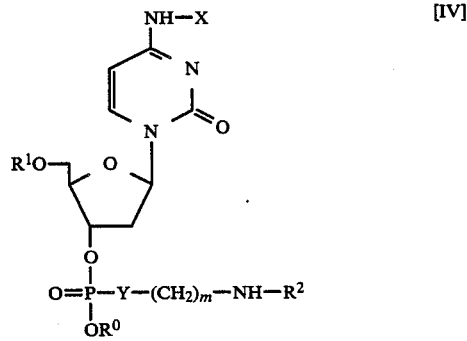

wherein: X is hydrogen or $-CO-(CH_2)_n-CO-R^3$; each of m and n is an integer up to 20; $R^0$ is a protective group of phosphoric acid group; $R^1$ is hydrogen or a protective group for 5'-hydroxyl group; $R^2$ is hydrogen or a protective group for amino group; $R^3$ is a carrier having an amino group as the functional group and bound at this functional group in this compound; and Y is an oxygen atom ($-O-$) or an imino group ($-NH-$).

The nucleotide of the present invention, when it is a compound where the X is $-CO-(CH_2)_n-CO-R^3$ and has a carrier through a spacer on extension from the amino group of deoxycytidine, can be used as the starting material for the synthesis of 3'-end aminated oligonucleotide according to the solid phase method, that is, the resin. Here, the resin is merely a carrier, but the compound of the present invention carried on the resin is nothing but the resin itself in appearance, and the compound carried on the resin may sometimes be called merely "resin". Accordingly, in the synthesis of a 3'-aminoalkylated oligonucleotide by the use of the present invention, the following effects can be obtained.

(1) Since the reaction scale can be made small, it is economical. That is, since a minute quantity (of the order of a few micrograms) of the oligonucleotide to be utilized for non-radioactive affinity probe is sufficient, waste can be obviated by making the reaction scale smaller.

(2) Since it is not required to purify the intermediates in the respective synthetic stages of the oligonucleotide, the synthesis operations can be simple, and the skill of an expert is not required for synthesis operations. Therefore, synthesis of a 3'-end aminated oligonucleotide is possible within a short time, whereby power saving and cost reduction can be realized.

Furthermore, by the use of such resin, the solid phase oligonucleotide synthesis is possible by using it as the solid support, and it is another feature of the present invention that such a possibility can also be obtained. Since the operation of synthesis of the oligonucleotide in this case is simple, automation or mechanical processing may also be feasible.

DETAILED DESCRIPTION OF THE INVENTION

Nucleotide (Compound [IV])

The nucleotide according to the present invention is represented by the above formula [IV]. Hereinafter, this nucleotide is called Compound [IV]. Symbols of the formula [IV] have the following meanings.

—$(CH_2)_m$—: an alkylene group, in which m is a natural number up to 20, which is practically 2 to 20, particularly preferably 2 to 8.

—CO—$(CH_2)_n$—CO—: a spacer, in which n is a natural number up to 20, which is practically 2 to 20, particularly preferably 3 to 8.

$R^0$: a substituent for protection of phosphoryl group, as exemplified by ortho- or para-chlorophenyl group, phenylthio group, and 5-chloro-8-oxyquinolyl group; generally, ortho-chlorophenyl group is used.

$R^1$: hydrogen or a protective group for a 5'-end hydroxyl group; when this is a protective group, it can be, for example, trityl, mono- or di-methoxytrityl group, trimethylacetyl group, and trioxyacetyl group; as the protective group, dimethoxytrityl group is generally used.

$R^2$: hydrogen or a protective group for an amino group; when this is a protective group, it can be, for example, trifluoroacetyl group and ortho-nitrosulphenyl group; as the protective group, trifluoroacetyl group is generally used.

$R^3$: a carrier which has an amino group as the functional group on it and is bound at the amino group with the nucleotide moiety; generally, amino-lower-alkylated (particularly aminomethylated) polystyrene, amino-lower-alkylated (particularly aminopropylated) silica gel and amino-lower-alkylated (particularly aminoethylated) polyacrylmorpholide are used.

Here, "polystyrene" and "polyacrylmorpholide" include not only respective homopolymers of styrene and acrylmorpholide but also respective copolymers thereof. Accordingly, for example, polyacrylmorpholide is ordinarily a copolymer of acrylamide and acrylmorpholide, as derived from the ordinary preparation method thereof by N-morpholide modification of polyacrylamide. On the other hand, N-lower-alkylated product of polyacrylmorpholide is a polymer in which at least a part of acrylmorpholide units are converted to N-aminoethylacrylamide, as derived from the ordinary preparation thereof by amide exchange of such a polyacrylmorpholide with ethanolamine. $R^3$ is the same as the solid carrier to be used in the solid phase synthetic method which is one of the methods for synthesizing oligonucleotides from its monomer. Details of such solid phase synthetic methods are described in, for example, Nucleic Acids Res. 8, 5473 (1980); ibid. 8, 5491 (1980); and ibid. 8, 5507 (1980).

Synthesis of Compound [IV]

Compound [IV], namely, the nucleotide according to the present invention, can be synthesized by any desired method suited for the object.

Figure 1:
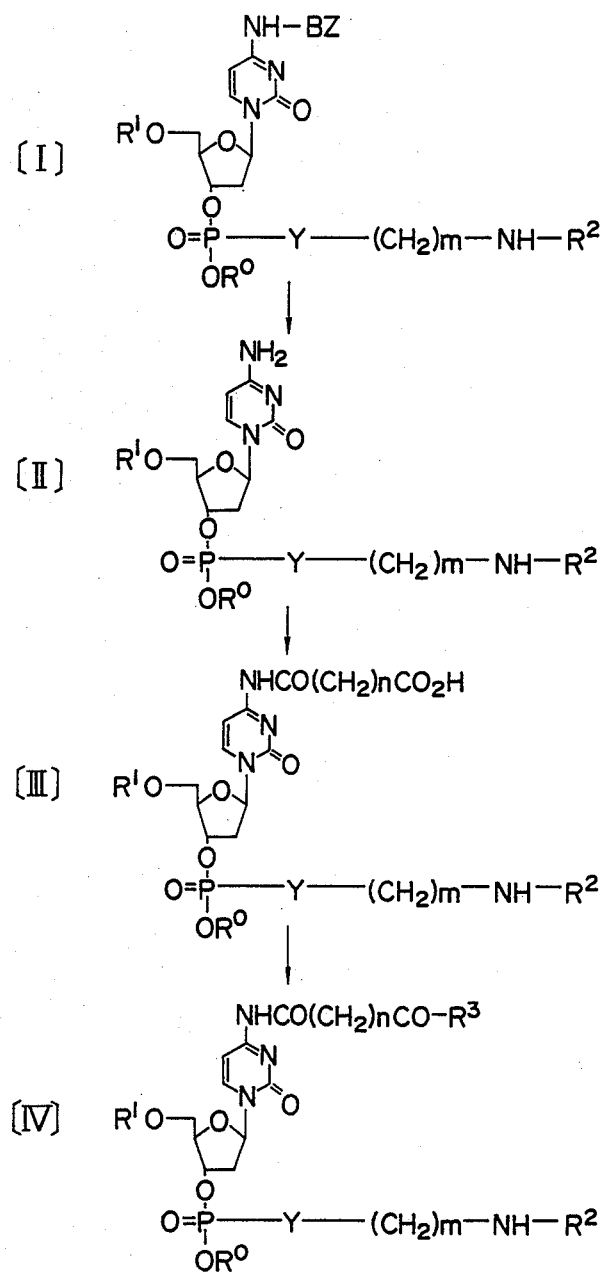
FIG. 1 is a flow chart showing an example of the method for synthesizing Compound [IV] of the present invention.

One preferable method is as shown in the flow chart in FIG. 1, $R^0$–$R^3$ have the meanings as described above, and BZ designating a benzoyl group.

The preferable method for synthesis of Compound [IV] is described below with reference to FIG. 1.

First, a cytidine derivative [I] completely protected is synthesized according to the method applied for ordinary nucleotide synthesis or according to the method I have previously proposed [Japanese Patent Application No. 22475/1984]. Next, in Compound [I], the protective group of the amino group at the base moiety is selectively eliminated to obtain Compound [II]. Selective elimination of the protective group at the base moiety may be done according to, for example, the method of Tetrahedron Letter, 22, 991–994 (1981). More specifically, Compound [I] can be treated with ethylenediamine in a reaction solvent to obtain Compound [II]. As the reaction solvent, dichloromethane, trichloromethane, N,N-dimethylformamide, etc. may be considered, but ethylenediamine-phenol [1:4(v/v)] is preferred in that decomposition of ortho-chlorophenyl group as recommended for $R^0$ is the smallest.

After preparation of Compound [III] by introduction of a spacer into the amino group at the base moiety of Compound [II] liberated by the above operation, this can be immobilized onto a carrier to obtain Compound [IV]. More specifically, introduction of a spacer (which may be a dicarboxylic acid having 2 to 20 carbon atoms, particularly preferably adipic acid, glutaric acid) is carried out in pyridine with the use of a condensing agent [e.g., dicyclohexylcarbodiimide (hereinafter abbreviated as DCC)] to obtain Compound [III]. Then, by binding Compound [III] to a carrier through the spacer introduced on extension from the amino group at the cytosine moiety of Compound [III], Compound [IV] is obtained. For example, by binding Compound [III] with a carrier having amino group as the functional group (e.g., aminomethylated polystyrene) in pyridine with the use of a condensing agent (e.g., DCC), Compound [IV] can be obtained. The general methods for nucleotide synthesis have already been known, and as for details of the kinds of protective groups, introduction, elimination and condensation thereof, or other pertinent matters, reference is made to textbooks or reviews concerning chemical synthesis of nucleic acids, for example, Tetrahedron 34, 31 (1978); Tetrahedron Letters 1979, 3635 (1979); Nucleic Acids Research 8, 5473 (1980); ibid. 8 5491 (1980); ibid. 8, 5507 (1980); and Nucleic Acids Research Symposium Series 7, 281 (1980). As for details of synthetic operations of Compound [IV], reference is made to the experimental examples set forth hereinafter.

Utilization of Compound [IV]/Synthesis of Oligonucleotide Derivative

The compound of the present invention (formula [IV]), as described above, is useful as the starting material for synthesis of a 3'-end aminated oligonucleotide according to the solid phase method.

Synthesis of a 3'-end aminated oligonucleotide by use of the Compound [IV] of the present invention can be performed according to any desired method suited for the object, by the use of the Compound [IV] as the resin to be used for the solid phase synthetic method, by condensing successively dimers, trimers or oligomers as nucleric acid reagents with the resin.

Figure 2:
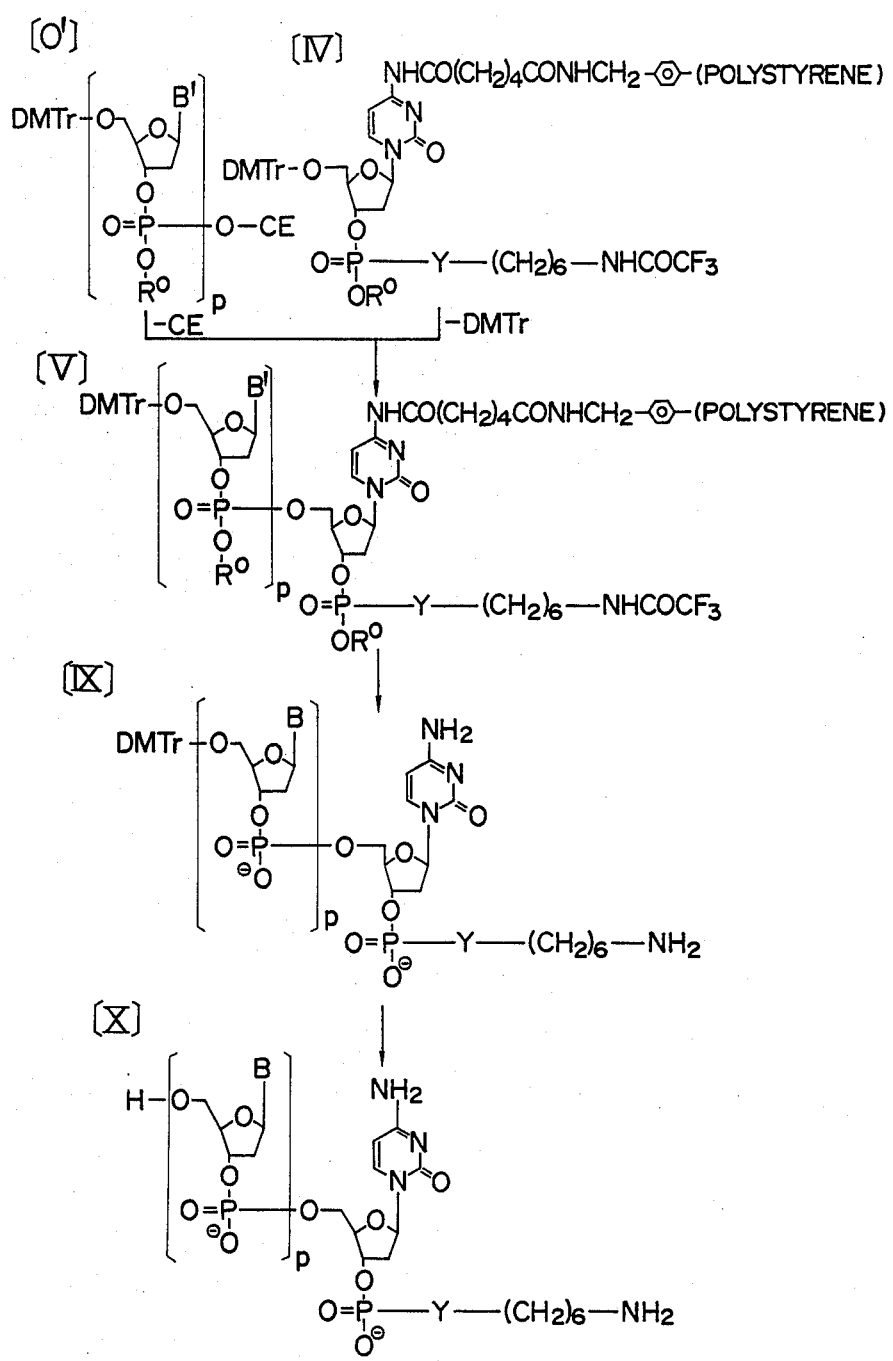
FIG. 2 is a flow chart showing an example of the method for synthesizing an oligonucleotide derivative [X] by the use of Compound [IV] of the present invention.

A preferable method is demonstrated in the flow chart in FIG. 2. The symbols in the flow chart have the following meanings:
CE: cyanoethyl group;
DMTr: dimethoxytrityl group;
p: any natural number, which is usually 1 to 100, preferably 1 to 40;
q: any natural number, which is usually 1 to 10, preferably 1 to 4;
B': protected base, generally selected from $N^6$-benzoyladenine, N-isobutyrylguanine, $N^6$-benzoylcytosine and thymine (that is, no protection required);
B: base, generally selected from adenine, guanine, cytosine and thymine; and
$R^0$, $R^1$, $R^2$, $R^3$, Y, m and n: the same meanings as stated hereinbefore.

A method for synthesis of a 3'-end aminated oligonucleotide is described below.

Compound [IV] from which DMTr has been removed and Compound [O'] synthesized by the conventional oligonucleotide synthetic method from which CE has been removed are bound in the presence of a condensing agent [e.g., mesitylenesulfonylnitrotriazolide (hereinafter abbreviated MSNT)] to obtain Compound [V]. By appropriately repeating this operation, a desired chain length can be obtained, and then elimination of the Compound [V] from the carrier [elimination operation can be performed by alkali treatment, generally by the use of conc. ammonia; in experimental examples, also, conc. ammonia treatment was performed, and the protective groups of the base group moiety and the phosphate group and trifluoroacetyl groups were also removed together with elimination from the carrier] produces Compound [IX], followed by removal of the protective group of 5'-hydroxyl group [removal of the protective group may be accomplished by acid treatment, for example, 0.1 N hydrochloric acid treatment or 80% acetic acid treatment, generally the latter] to obtain Compound [X].

Similarly as described above, Compound [VIII] having aminoalkyl groups introduced at 5'- and 3'-ends can be obtained. A preferable example of synthesis of Compound [VIII] is shown in the flow chart in FIG. 3. The symbols in this Figure have the same meanings as set forth hereinbefore.

More specifically, synthesis of Compound [VIII] is performed by first binding Compound [O] prepared according to the conventional oligonucleotide synthetic method which has been subjected to decyanoethylation with Compound [IV] of the present invention from which $R^1$ (DMTr) has been removed in the presence of a condensing agent to obtain Compound [V] with a desired chain length. Next, by carrying out binding of Compound [VI] synthesized according to the method disclosed in Japanese Patent Laid-Open Publication No. 93098/1984, which has been subjected to decyanoethylation with Compound [IV] from which $R^1$ (DMTr) hs been removed, Compound [VII] is obtained. Finally, deprotection of Compound [VII] and elimination from the carrier are carried out to produce Compound [VIII]. Concerning the solid phase methods for synthesis of oligonucleotide, there are various textbooks and literatures. For example, reference may be made to the following literatures, published patent specifications and experimental examples:
Tetrahedron Letters 1979, 3635 (1979);
Nucleic Acids Research 8, 5473 (1980);
Nucleic Acids Research 8, 5491 (1980);
Nucleic Acids Research 8, 5507 (1980);
Nucleic Acids Research Symposium Series 7, 281 (1980); and
Japanese Patent Laid-Open Publications Nos. 27900/1984, 93098/1984, 93099/1984 and 93100/1984.

The 3'-end aminated oligonucleotide thus synthesized can also be bound to a label through the primary amino group (Ref.: Japanese Patent Laid-Open Publication No. 148798/1984 and Japanese Patent Application No. 75878/1983).

Experimental Examples

A. Synthesis of Compound [IV]

Synthesis of Compound [IV] of the present invention was carried out following the procedure as described below.

(1) Synthesis of Compound [I] (Y=O)

Figure 4:
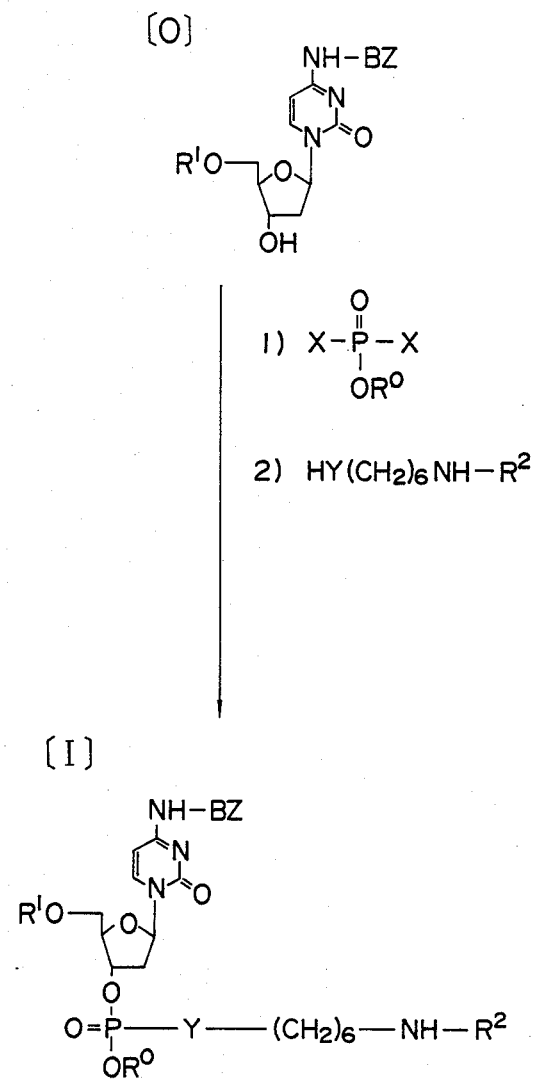
FIG. 4 is a flow chart showing an example of the method for synthesizing the compound [I] used for synthesis of Compound [IV] of the present invention.

Synthesis of Compound [I] (Y=O) was carried out by following the flow chart shown in FIG. 4 (the symbol X in the Figure representing a halogen, triazole or hydroxybenzotriazole, and other symbols having the meanings as stated hereinbefore). That is, the Compound [O] (890 mg, 1.4 mmol) made anhydrous by pyridine azeotropy and a dioxane solution of ortho-chlorophenyl phosphodibenzotriazolide (the compound wherein X is hydroxybenzotriazole) (7 ml/mM, 12.6 ml) were added, and the reaction was carried out for 2 hours. After completion of the reaction was confirmed by thin layer chromatography (hereinafter abbreviated TLC), trifluoroacetyl-6-aminohexanol [Y=O, $R^2$=CF$_3$CO] (530 mg, 2.5 mM) made anhydrous by pyridine azeotropy and toluene azeotropy and 1-methyl-imidazole (200 μl, 2.5 mM) were added, and the reaction was carried out at room temperature overnight.

After completion of the reaction, the solvent was evaporated, and the residue was dissolved in 30 ml of chloroform (hereinafter written as CHCl$_3$), washed with water, 0.5 M sodium dihydrogen phosphate (hereinafter written as NaH$_2$PO$_4$) and 5% sodium hydrogen carbonate (hereinafter written as NaHCO$_3$), and then dried over anhydrous sodium sulfate (hereinafter written as Na$_2$SO$_4$). The CHCl$_3$ layer was concentrated and purified through a silica gel short column to obtain the desired Compound [I] (Y=O) [Yield: 910 mg (1.14 mM), 81%].

Elution of the desired product from the silica gel column was performed with an eluant having a gradient of CHCl$_3$ containing 0–4% of methanol [hereinafter this expression being shown as "MeOH/CHCl$_3$(0–4%)"].

This compound was confirmed by nuclear magnetic resonance spectrum (hereinafter abbreviated NMR).

NMR (CDCl$_3$): δ=8.12 (dd 1H), 6.30 (m 1H), 5.30 (t 1H), 4.20 (m 2H), 3.78 (s 6H), 3.33 (m 2H), 1.40 (m 4H).

(1') Synthesis of Compound [I] (Y=NH)

Similarly as described above, synthesis of Compound [I] (Y=NH) was carried out. That is, after Compound [O] (1.32 g, 2 mmol) was made anhydrous, a dioxane solution of ortho-chlorophenyl phosphodibenzotriazolide (6 ml/mM, 16.8 ml) was added thereto, and the reaction was carried out for 2 hours. To the resultant mixture were added monotrifluoroacetyl-1,6-diaminohexane [Y=NH, $R^2$=CF$_3$CO] hydrochloride (900 mg, 3.6 mM) and 1-methyl-imidazole (440 mg, 5.6 mM), and the reaction was conducted overnight. Following, subsequently, the same procedure as described above, the desired Compound [I] (Y=NH) was obtained in a yield of 710 mg (44%). This compound was also confirmed by NMR.

NMR (CDCl$_3$): δ=8.13 (dd 1E), 6.34 (t1H), 5.28 (m 1H), 3.77 (s 6H), 3.32 (m 2H), 3.00 (m 2H), 1.34 (m 4H).

(2) Synthesis of Compound [II] (Y=O)

Compound [I] (Y=O) (550 mg, 0.7 mM) was dissolved in 15 ml of ethylenediamine-phenol (1:4 (v/v)), and the reaction was carried out at 40° C. for 30 minutes. After confirmation of completion of the reaction by TLC, the solution was concentrated. The residue was dissolved in CHCl$_3$, then washed with 0.5 MNaH$_2$PO$_4$, 5% NaHCO$_3$, 5% sodium chloride (hereinafter written as NaCl) and water, and dried over anhydrous Na$_2$SO$_4$. After evaporation of CHCl$_3$, the product was purified through a silica gel short column [MeOH/CHCl$_3$(0–3%)]. Then, the purified product was added dropwise into pentane to obtain a powder of Compound [II], (yield: 360 mg, 54%). The compound of the present invention was confirmed by NMR.

NMR (CDCl$_3$): δ=7.77 (t 1H), 6.34 (q 1H), 5.54 (dd 2H), 5.26 (m 1H), 4.19 (m 2H), 3.77 (s 6H), 3.31 (t 2H), 1.37 (m 4H).

(3) Synthesis of Compound [III] (Y=O)

In a solution of Compound [II] (Y=O) (100 mg, 0.11 mmol) dissolved in anhydrous pyridine (2 ml), adipic acid (50 mg, 0.34 mmol) and dicyclohexylcarbodiimide (hereinafter written as DCC) (140 mg, 0.68 mmol) were added, and the reaction was carried out at room temperature. After confirmation of completion of the reaction by TLC, the reaction mixture was filtered and the filtrate was concentrated. Then, the concentrate was dissolved in CHCl$_3$, and washed with water, 5% NaHCO$_3$ and 5% NaCl. Then, the CHCl$_3$ layer was concentrated, dissolved in a small amount of benzene and added dropwise into pentane to obtain a crude product of Compound [III] (Y=O) as powder, (yield: 90 mg, 80%). The crude product was used as it was in the next reaction.

(4) Synthesis of Compound [IV] (Y=O)

Compound [III] (Y=O) (90 mg, 0.086 mmol) was added to a pyridine solution (4 ml) containing an aminomethylated polystyrene resin (0.12 mmol/g) (commercial product) suspended therein, after which DCC (60 mg, 0.3 mmol) was added, and the reaction was carried out at room temperature overnight. After completion of the reaction, the resin was washed with pyridine, and the reaction was carried out with addition of 5 ml of acetic anhydride-pyridine (1:9 (v/v)) for one hour thereby to protect the unreacted amino group with an acetyl group. After washing with methanol, the product was dried to obtain Compound [IV] (420 mg). Here, the cytidine content was calculated by quantitative determination of trityl groups by sampling a small amount of Compound [IV] to be 0.046 mmol/g.

In addition, Compound [IV] (Y=O) was synthesized according to the above method by using the purified Compound [III] (Y=O) [10 mg, 9 μmol], an aminomethylpolystyrene resin (0.13 mmol/g, 40 mg), and DCC (20 mg, 10 μmol). In this case, the cytidine content was found to be 0.096 mmol/g from quantitative determination of the trityl groups similarly as described above.

On the other hand, Compound [IV] (Y=NH) also could be obtained according to the above method.

B. Synthesis of Oligonucleotide

By the use of the compound of the present invention (formula [IV] ), synthesis of an oligonucleotide was carried out.

(a) Synthesis of Compound [X] (Y=O, B=T, p=12)

Synthesis of the above Compound [X] was carried out by following the flow chart shown in FIG. 2. That is, the resin [IV] (Y=O) (20 mg, 0.096 mmol/g, 1.9 μmol) (here, the resin is merely a carrier, but the compound of the present invention carried on the resin is nothing but the resin itself in appearance, and hence this compound carried on the resin is called merely the resin) was (i) washed (x 5) with 1 ml of dichloromethane (hereinafter written as CH$_2$Cl$_2$) and thereafter (ii) the reaction with the use of 1 ml of CH$_2$Cl$_2$ containing 3% trichloroacetic acid (hereinafter written as 3% TCA/CH$_2$Cl$_2$) for 20 seconds were repeated 6 times as a total.

The thus detritylated Compound [IV] was subjected to (iii) washing with 1 ml of CH$_2$Cl$_2$ (x 5) and 1 ml of pyridine (x 5), further washed with 1 ml of $CH_2Cl_2$ (x 5), and then vacuum dried. Subsequently, (iv) the reaction was carried out for 40 minutes with addition of 300 μl of an anhydrous pyridine solution of 25 mg of a condensing agent mesitylenesulfonylnitrotriazolide (hereinafter written as MSNT) and 25 mg of decyanoethylated thymidine dimer (the Compound [0'] where p=2, B'=T).

After completion of the reaction, the resin was (v) washed with 1 ml of pyridine (x 5), and (vi) the reaction was carried out for 5 minutes with addition of 1 ml of acetic anhydride-pyridine-dimethylaminopyridine (hereinafter written as DMAP) [100 μl–900 μl –10 mg] to acetylate the unreacted 5'-hydroxyl group, followed by (vii) washing with 1 ml of pyridine (x 5), thus completing one cycle of condensation operation. Subsequently, by using the decyanoethylated thymidine dimer, the above condensation operation of (i)—(vii) was repeated five times to obtain Compound [V] (Y=O, B=T, p=12). The yield was 57% as an overall by quantitative determination of trityl groups (91% on average).

Figure 5:
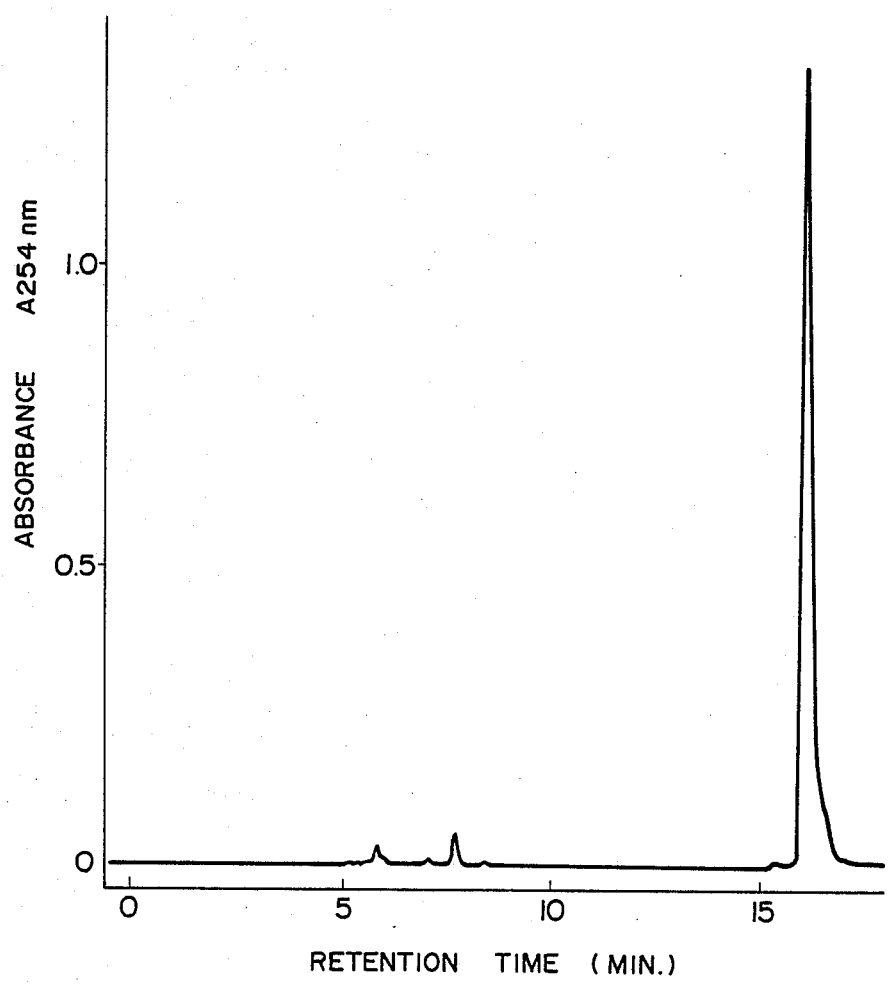
FIG. 5 is a reproduction of the chromatogram obtained when the compound [IX] obtained in the experiment B-(a) is purified by separation by HPLC.

Then, Compound [V] was dissolved in 300 μl of a pyridine-water (9:1 (v/v)) solution of 0.5 M tetramethylguanidine-pyridine-2-carboaldoxime, treated at room temperature overnight, and then, with addition of conc. ammonia water (3 ml) to the solution, further treated at 50° C. overnight under tight sealing. After the treatment, the resin was filtered off, and the filtrate was concentrated. The residue was dissolved in 1 ml of 50 mM tetraethylammonium bicarbonate (hereinafter written as TEAB) pH 7.5 and washed (x 3) with 1 ml of ether. The aqueous layer was concentrated, then dissolved in TEAB and its half amount was applied onto Sephadex ® G - 50 (diameter 1.5 cm × length 120 cm, eluant 50 mM TEAB) for crude purification to obtain a crude product 6.0–9.0 OD of Compound [IX] (Y=O, B=T, p=12). This was then purified by separation by high performance liquid chromatography (hereinafter abbreviated HPLC) by using a reversed phase column, elution pattern of which is shown in FIG. 5.

Figure 6:
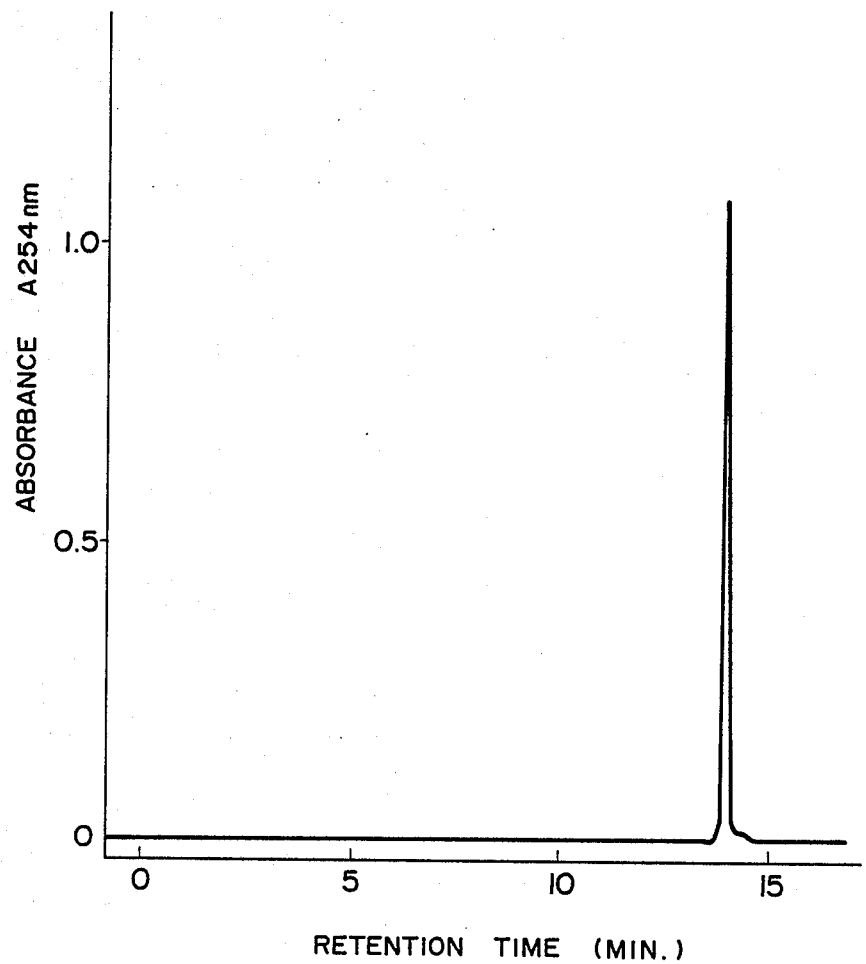
FIG. 6 is a reproduction of the chromatogram obtained when the compound [X] in the experiment B-(a) is purified by separation by HPLC.

The Compound [IX] separated by HPLC was treated with 80% acetic acid for 10 minutes and again subjected to purification by separation by HPLC to obtain Compound [X] (Y=O, B=T, p=12) (the elution pattern is shown in FIG. 6). In FIG. 5 and FIG. 6, each elution pattern exhibits a single peak, which indicates that each of Compounds [IX] and [X] could be obtained in pure form.

Confirmation of Compound [X] was also performed by carrying out polyacrylamide gel electrophoresis after labelling the compound with $^{32}p$.

The above HPLC was conducted under the following conditions.

Column: μBondapak C 18
Temperature: 50° C.
Flow rate: 2 ml/min.
Eluant A: 50 mM triethylammonium acetate (hereinafter abbreviated TEAA) pH 7.2 B: 50 mM TEAA (pH 7.2) - acetonitrile ($CH_3CN$) (1:1 (v/v)).

In the case of Compound [IX], a linear concentration gradient of 20 to 60% of the eluant B was employed, and the elution time was 16 minutes. Such a condition is hereinafter written as (20→60% B buffer/16 minutes). On the other hand, in the case of Compound [X], it was (0→40% B buffer/16 minutes).

(b) Synthesis of Compound [X] (Y=O, B=A, p=12)

Figure 7:
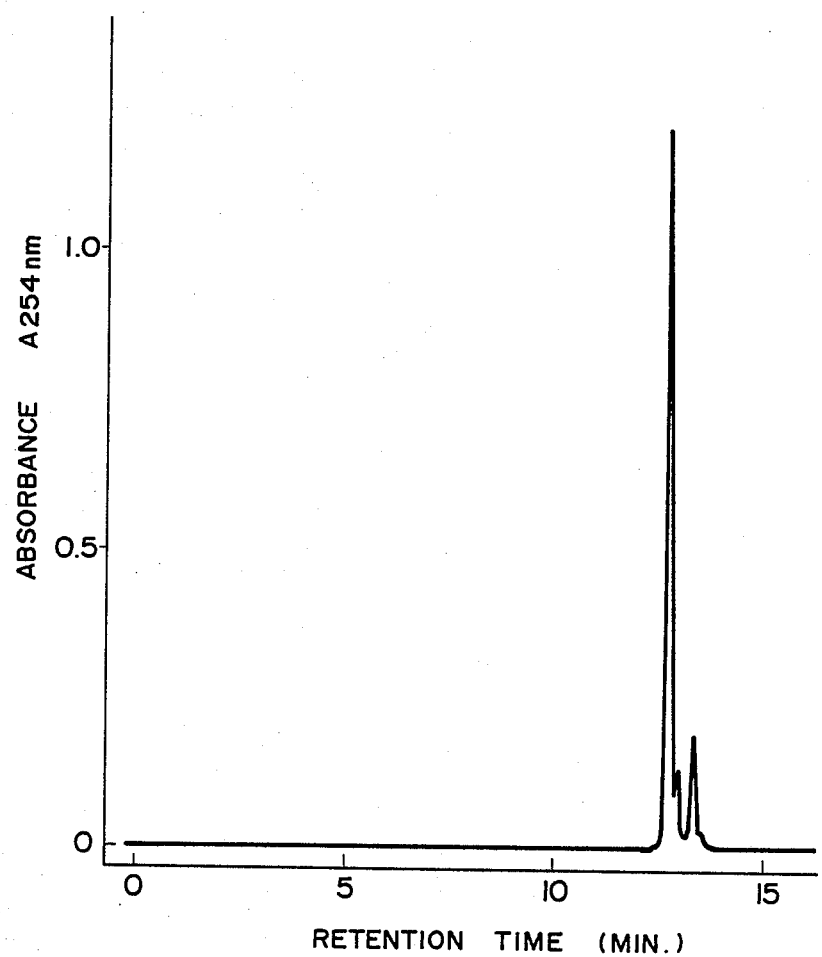
FIG. 7 is a reproduction of the chromatogram obtained when the compound [X] in the experiment B-(b) is purified by separation by HPLC.

By the use of the resin [V] (40 mg, 0.046 mmol/g, 1.8 μmol) and a solution of adenosine dimer (25 mg) dissolved in anhydrous pyridine (400 μl) as the nucleic acid reagent, synthesis of Compound [X] was carried out following the operations (i) through (vii) of the above experiment (a) (average yield 90%). FIG. 7 is the elution pattern when Compound [X] in this experiment (b) was purified by separation by HPLC (0→40% B buffer/16 min.).

(c) Synthesis of Compound [X] (Y=O, p=14, see Table 1 for B)

Figure 8:
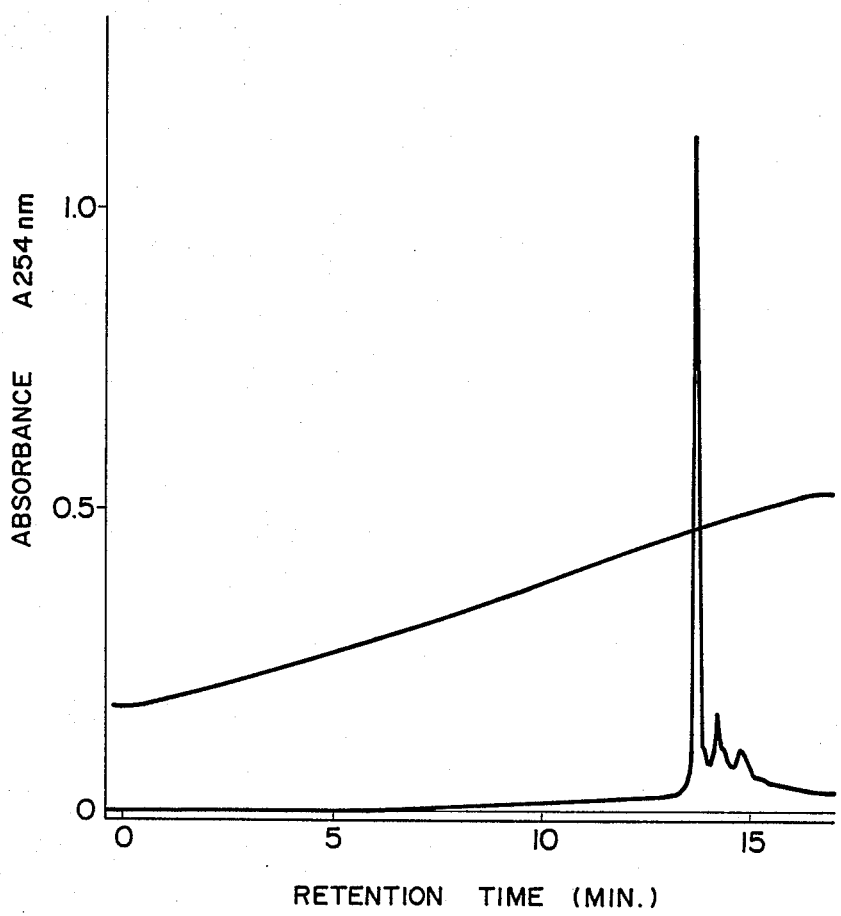
FIG. 8 is a reproduction of the chromatogram obtained when the compound [X] in the experiment B-(c) is purified by separation by HPLC.

By the use of the resin [IV] (100 mg, 0.046 mmol/g, 4.6 μmol) and solutions of various dimers (GC, TA, TG, GA, CC, CA and TT being condensed in this order) dissolved in anhydrous pyridine (800 ml) as nucleic acid reagents, synthesis of Compound [X] was carried out following otherwise the operations (i) through (vii) in the above experiment (a). FIG. 8 is the elution pattern when Compound [X] in this experiment was purified by separation by HPLC (0→40% B buffer/16 min.).

The contents of the compounds synthesized in the above experiments (a), (b) and (c) are shown in Table 1.

TABLE 1

| Experiment | Compound [X] Symbol in the formula [X] | | | | | | | | | | | | | |
|---|---|---|---|---|---|---|---|---|---|---|---|---|---|---|
| | p | Y | B | | | | | | | | | | | |
| a | 12 | O | T | T | T | T | T | T | T | T | T | T | T | |
| b | 12 | O | A | A | A | A | A | A | A | A | A | A | A | |
| c | 14 | O | T | T | C | A | C | C | G | A | T | G | T | A G C |

In the above Table and the above sentences, T is thymine, A is adenine, G is guanine, C is cytosine, which are symbols accepted in the field of the art to which the present invention belongs.

(d) Synthesis of Compound [VIII] (Y=O, B=indicated in Table 2, m=6, p+q=14)

Figure 3:
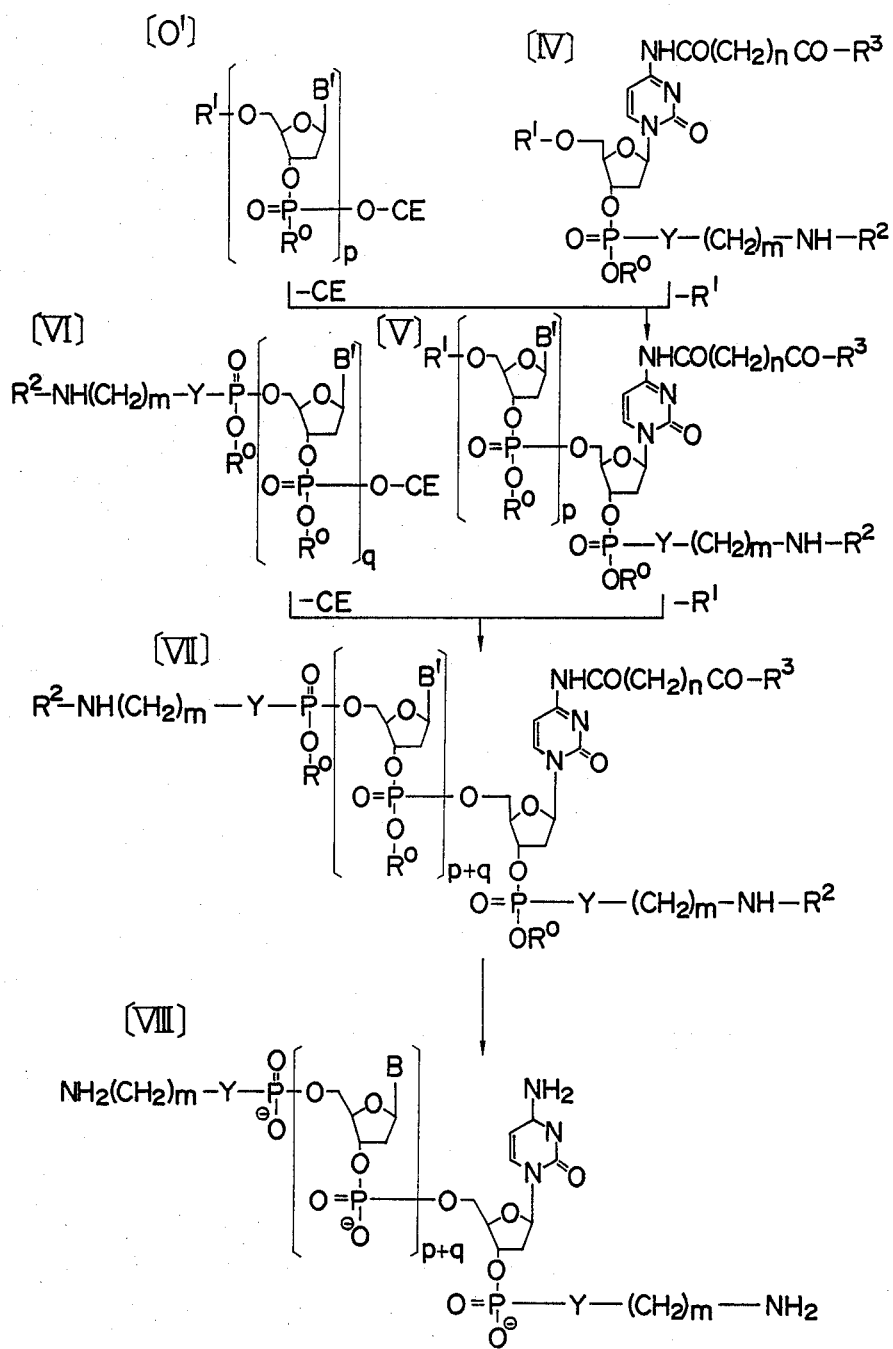
FIG. 3 is a flow chart showing an example of the method for synthesizing an oligonucleotide derivative [VIII] by the use of Compound [IV] of the present invention.

By following the flow chart in FIG. 3, Compound [VIII] (Y=O, B=indicated in Table 2, m=6, p+q=14) was synthesized.

(i) Synthesis of Compound [V]

According to the same method as in the above experiments (a), (b), and (c), synthesis of Compound [V] ($R^1$=DMTr, $R^2$=$CF_3CO$-, Y=O, B=CACCGATGTAGC, p=12, m=6, n=4) was carried out.

(ii) Synthesis of Compound [VI]

Compound [O'] ($R^1$=H, B'=T, $R^0$-ortho-chlorophenyl, p=2) [450 mg, 0.5 mmol] was rendered anhydrous by pyridine azeotropy. A dioxane solution (0.7 mmol) of ortho-chlorophenyl phosphodibenzotriazolide was added thereto, and the reaction was carried out for 2 hours. After confirmation of the progress of the reaction by TLC, trifluoroacetyl-6-aminohexanol (190 mg, 0.9 mmol) and 1-methyl-imidazole (75 mg, 0.9 mmol) were added to the reaction mixture, and the reaction was further carried out for 3 hours. After completion of the reaction, the solution was concentrated, and the concentrate was dissolved in CHCl$_3$, washed with water, 5% NaHCO$_3$, 0.5 M NaH and 5% NaCl, and dried over anhydrous Na$_2$SO$_4$. Then, the CHCl$_3$ layer was concentrated and purified through a silica gel short column to obtain Compound [VI] (R$^O$=ortho-chlorophenyl, R$^2$=CF$_3$CO, B'=T, q=2). The product was added dropwise into npentane to be formed into a powder [Yield: 460 mg (72%)].

(iii) Synthesis of Compound [VIII]

Next, Compound [V] from which DMTr had been removed and Compound [VI] from which CE had been removed were condensed together in the presence of MSNT to obtain Compound [VII] (R$^0$=ortho-chlorophenyl, R$^2$=CF$_3$CO, R$^3$aminomethylated polystyrene, n=4, m=6, p+q=14, Y=O). Then, after all of the protective groups were eliminated according to the conc. ammonia treatment and the 80% acetic acid treatment similarly as in the above experiment (a), this compound was purified by HPLC to obtain Compound [VIII] (Y=O, p+q=14, m=6).

Figure 9:
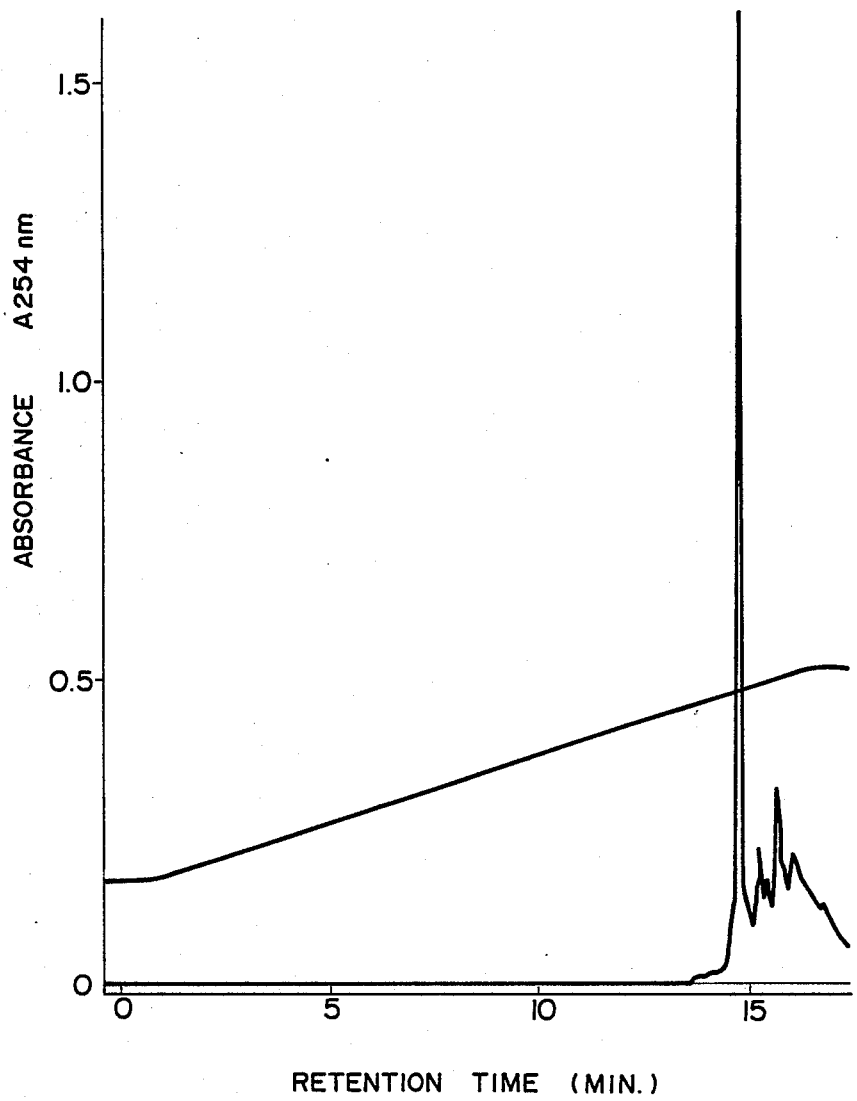
FIG. 9 is a reproduction of the chromatogram obtained when the compound [VIII] in the experiment B-(d) is purified by separation by HPLC.

The elution pattern of Compound [VIII] in HPLC was as shown in FIG. 9. In this pattern, peaks of impurities can be seen, but by collecting only the fraction of the main peak separated by HPLC, the desired compound was obtained in pure form.

(e) Synthesis of Compound [VIII] (Y on 5'-side=NH, Y on 3'-side=O, p+q=13, m=6)

Figure 10:
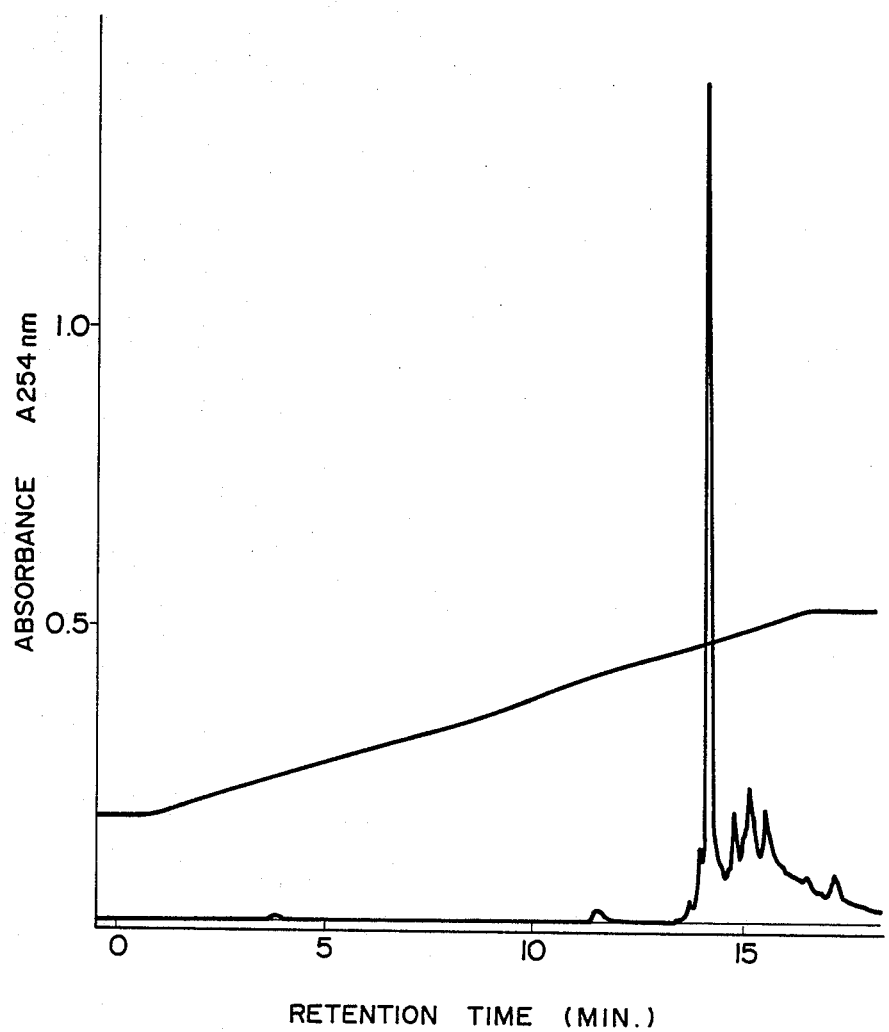
FIG. 10 is a reproduction of the chromatogram obtained when the compound [VIII] in the experiment B-(e) is purified by separation by HPLC.

To Compound [O'] (R$^0$=ortho-chlorophenyl, R$^1$=H, B'=T, p=1) (1 mmol, 480 mg) rendered anhydrous by pyridine azeotropy was added a dioxane solution of orthchlorophenyl phosphodibenzotriazolide (1.4 mmol), and the reaction was carried out for one hour. Then, to the reaction mixture were added mono-trifluoroacetyl- 1,6-diaminohexane hydrochloride (1.8 mmol, 450 mg) rendered anhydrous and 1-methyl-imidazole (2.8 mmol, 220 mg), and the reaction was carried out for 2 hours. Subsequently, following the same procedure as in (ii) in the experiment (d), Compound [VI] was obtained. Next, by the use of Compound [VI] and Compound [V] obtained in (i) in the experiment (d), Compound [VIII] (see Table 2) was obtained according to the same procedure as in (iii) in the experiment (d). FIG. 10 is the elution pattern when Compound [VIII] was purified by HPLC. In this pattern, peaks of impurities can be seen, but by collecting only the fraction of the main peak separated by HPLC, the desired compound was obtained in pure form.

The contents of the compounds synthesized in the experiments (d) and (e) are shown in Table 2.

What is claimed is:
1. A nucleotide of the formula:

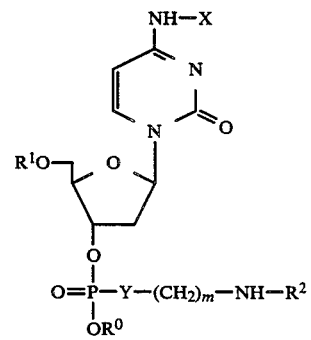

wherein
X is hydrogen or —CO(CH$_2$)$_n$—CO—R$^3$; wherein each of m and n is a natural number up to 20; and
R$^o$ is selected from the group consisting of ortho-chlorophenyl, para-chlorophenyl, phenylthio and 5'-chloro-8-oyquinoly;
R$^1$ is hydrogen or a protective group of a 5'-end hydroxyl group selected from the group consisting of trityl, monomethoxy-trityl, di-methoxytrityl, and trimethyl acetyl and
R$^3$ is an amino-lower alkylated polystyrene, an amino-lower alkylated silica gel or an aminated polyacrylomorpholide; and wherein R$^2$ is hydrogen or a protective group for an amino group; and Y is an oxygen atom (-0-) or an imino group (-NH-).

2. The nucleotide according to claim 1, wherein X is hydrogen.

3. The nucleotide according to claim 1, wherein X is —CO—(CH$_2$)$_n$—CO—.

4. The nucleotide according to claim 1, wherein R$^0$ is an ortho-chlorophenyl group.

5. A nucleotide according to claim 1, wherein R$^1$ is hydrogen.

6. The nucleotide according to claim 1, wherein R$^1$ is a trityl group, a mono-methoxytrityl group, a di-methoxytrityl group, or a trimethylacetyl group.

7. The nucleotide according to claim 6, wherein R$^1$ is a dimethoxytrityl group.

8. A nucleotide according to claim 1, wherein R$^2$ is hydrogen.

9. A nucleotide according to claim 1, wherein R$^2$ is a trifluoroacetyl group or an ortho-nitrosulphenyl group.

10. The nucleotide according to claim 9, wherein R$^2$ is a trifluoroacetyl group.

11. The nucleotide according to claim 1, wherein R$^3$ is an amino-lower-alkylated polystyrene, an amino-lower-alkylated silica gel or an aminated polyacrylmorpholide.

12. The nucleotide according to claim 1, wherein m is an integer of 2 to 8.

13. The nucleotide according to claim 1, wherein n is an integer of 2 to 8.

TABLE 2

| Experiment | p + q | Y | Compound [VIII] Symbol in the formula [VIII] B | | | | | | | | | | | | |
|---|---|---|---|---|---|---|---|---|---|---|---|---|---|---|---|
| d | 14 | O 5'-side | T | T | C | A | C | C | G | A | T | G | T | A | G | C |
| e | 13 | Y=NH 3'-side Y=O | | T | C | A | C | C | G | A | T | G | T | A | G | C |

14. A nucleotide of the formula:

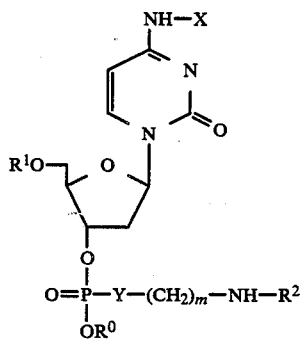

wherein

X is hydrogen or —CO(CH$_2$)$_n$—CO—R$^3$; wherein each of m and n is a natural number up to 20; and R$^o$ is selected from the group consisting of ortho-chlorophenyl, para-chlorophenyl, phenylthio and 5'-chloro-8-oxyquionolyl;

R$^1$ is hydrogen or a protective group for a 5'-end hydroxyl group selected from the group consisting of trityl, monomethoxytrityl, di-methoxytrityl, and trimethylacetyl; and R$^3$ is an amino-lower alkylated polystryrene, an amino-lower alkylated silica gel or an aminated polyacrylmorpholide and wherein R$^2$ is hydrogen or a protective group for an amino group, and Y is an oxygen atom (-O-) or an imino group (-NH-).

15. The nucleotide according to claim 14, wherein said protective group for an amino group for R$^2$ is a trifluoroacetyl or an ortho-nitrosulfenyl group.

* * * * *